US010265202B2

(12) United States Patent
Greenberg et al.

(10) Patent No.: US 10,265,202 B2
(45) Date of Patent: Apr. 23, 2019

(54) PROSTHESIS HAVING AN EVERTING PIVOTING FENESTRATION

(71) Applicants: Cook Medical Technologies LLC, Bloomington, IN (US); The Cleveland Clinic Foundation, Cleveland, OH (US)

(72) Inventors: Roy K. Greenberg, Bratenahl, OH (US); Blayne A. Roeder, Bloomington, IN (US); Matthew S. Huser, West Lafayette, IN (US); William J. Havel, West Lafayette, IN (US)

(73) Assignees: Cook Medical Technologies LLC, Bloomington, IN (US); The Cleveland Clinic Foundation, Cleveland, OH (US)

( * ) Notice: Subject to any disclaimer, the term of this patent is extended or adjusted under 35 U.S.C. 154(b) by 117 days.

(21) Appl. No.: 13/826,289

(22) Filed: Mar. 14, 2013

(65) Prior Publication Data

US 2014/0277335 A1    Sep. 18, 2014

(51) Int. Cl.
*A61F 2/07* (2013.01)
*A61F 2/856* (2013.01)
(Continued)

(52) U.S. Cl.
CPC ............... *A61F 2/856* (2013.01); *A61F 2/07* (2013.01); *A61F 2/954* (2013.01);
(Continued)

(58) Field of Classification Search
CPC ........ A61F 2002/061; A61F 2/07; A61F 2/89; A61F 2002/821; A61F 2250/0039; A61F 2/856
(Continued)

(56) References Cited

U.S. PATENT DOCUMENTS 1,597,525 A    8/1926    Knake
5,366,473 A    11/1994   Winston et al.
(Continued)

FOREIGN PATENT DOCUMENTS

EP    1673039    6/2006
EP    1847234    10/2007
(Continued)

OTHER PUBLICATIONS

Extended European Search Report, EP 14275040, search completed Apr. 25, 2014.
(Continued)

*Primary Examiner* — Katherine M Shi
(74) *Attorney, Agent, or Firm* — Brinks Gilson & Lione

(57) ABSTRACT

The present disclosure relates to an endoluminal prosthesis, such as a stent graft that includes one or more fenestrations to accommodate endovascular disease, such as an aneurysm in cases where one or more side branches is involved. In one aspect, the prosthesis includes fenestrations that are pivotable to accommodate the dynamic geometry of the aortic branches. In another aspect, the pivotable fenestrations include a first perimeter, a band of flexible material attached and surrounding the first perimeter, a second perimeter attached to and surrounding the band of flexible material and a support frame disposed about a surface of the band of flexible material. The first perimeter, band of flexible material, and second perimeter have a geometric shape. The support frame includes a plurality of support units having curved segments. The curved segments of the support units may be concave with respect to an exterior surface of the prosthesis.

8 Claims, 8 Drawing Sheets

(51) Int. Cl.
*A61F 2/954* (2013.01)
*A61F 2/06* (2013.01)

(52) U.S. Cl.
CPC ... *A61F 2002/061* (2013.01); *A61F 2002/075* (2013.01); *A61F 2250/0039* (2013.01)

(58) Field of Classification Search
USPC ...................................... 623/1.11, 1.13, 1.15
See application file for complete search history.

(56) References Cited

U.S. PATENT DOCUMENTS

| | | | |
|---|---|---|---|
| 5,425,765 | A | 6/1995 | Tiefenbrun et al. |
| 5,445,600 | A | 8/1995 | Abdulla |
| 5,603,698 | A | 2/1997 | Roberts et al. |
| 5,653,743 | A | 8/1997 | Martin |
| 5,662,703 | A | 9/1997 | Yurek et al. |
| 5,676,697 | A | 10/1997 | McDonald |
| 5,984,955 | A | 11/1999 | Wisselink |
| 6,086,526 | A | 7/2000 | Francischelli |
| 6,344,052 | B1 | 2/2002 | Greenan et al. |
| 6,395,018 | B1 | 5/2002 | Castaneda |
| 6,514,286 | B1 | 2/2003 | Leatherbury et al. |
| 6,524,335 | B1 | 2/2003 | Hartley et al. |
| 6,942,879 | B2 | 9/2005 | Humes |
| 7,678,141 | B2 | 3/2010 | Greenan et al. |
| 2002/0052648 | A1 | 5/2002 | McGuckin, Jr. et al. |
| 2002/0058992 | A1 | 5/2002 | Greenhalgh |
| 2002/0198585 | A1 | 12/2002 | Wisselink |
| 2003/0199967 | A1 | 10/2003 | Hartley et al. |
| 2004/0034406 | A1 | 2/2004 | Thramann |
| 2004/0059406 | A1 | 3/2004 | Cully et al. |
| 2004/0106972 | A1 | 6/2004 | Deaton |
| 2004/0215327 | A1 | 10/2004 | Doig et al. |
| 2005/0102021 | A1 | 5/2005 | Osborne |
| 2005/0131517 | A1 | 6/2005 | Hartley et al. |
| 2005/0131518 | A1 | 6/2005 | Hartley et al. |
| 2005/0149166 | A1 | 7/2005 | Schaeffer et al. |
| 2005/0171597 | A1 | 8/2005 | Boatman et al. |
| 2005/0171598 | A1 | 8/2005 | Schaeffer |
| 2005/0182476 | A1 | 8/2005 | Hartley et al. |
| 2005/0222668 | A1 | 10/2005 | Schaeffer et al. |
| 2005/0222669 | A1* | 10/2005 | Purdy ....................... A61F 2/07 623/1.13 |
| 2005/0228488 | A1 | 10/2005 | Nazzaro |
| 2005/0273155 | A1 | 12/2005 | Bahler et al. |
| 2006/0004436 | A1* | 1/2006 | Amarant et al. ............. 623/1.15 |
| 2006/0058864 | A1 | 3/2006 | Schaeffer et al. |
| 2006/0247760 | A1 | 11/2006 | Ganesan et al. |
| 2007/0244547 | A1 | 10/2007 | Greenan |
| 2007/0276468 | A1 | 11/2007 | Holzer et al. |
| 2008/0172123 | A1* | 7/2008 | Yadin ........................... 623/1.35 |
| 2009/0030502 | A1 | 1/2009 | Sun et al. |
| 2009/0164001 | A1 | 6/2009 | Biggs et al. |
| 2009/0240316 | A1 | 9/2009 | Bruszewski |
| 2009/0259290 | A1 | 10/2009 | Bruszewski et al. |
| 2009/0264821 | A1 | 10/2009 | Mafi et al. |
| 2009/0264991 | A1 | 10/2009 | Paul et al. |
| 2010/0063576 | A1 | 3/2010 | Schaeffer et al. |
| 2010/0268319 | A1* | 10/2010 | Bruszewski .............. A61F 2/07 623/1.13 |
| 2010/0268327 | A1 | 10/2010 | Bruszewski et al. |
| 2011/0054586 | A1 | 3/2011 | Mayberry et al. |
| 2011/0166644 | A1 | 7/2011 | Keeble et al. |
| 2012/0035714 | A1* | 2/2012 | Ducke ....................... A61F 2/07 623/1.34 |
| 2012/0046728 | A1* | 2/2012 | Huser et al. ................. 623/1.13 |
| 2012/0197382 | A1 | 8/2012 | Roeder |
| 2012/0221096 | A1 | 8/2012 | Roeder et al. |
| 2012/0271401 | A1* | 10/2012 | Bruszewski .............. A61F 2/07 623/1.15 |

FOREIGN PATENT DOCUMENTS

| | | |
|---|---|---|
| WO | 2005/034810 | 4/2005 |
| WO | 2009/056644 | 5/2009 |
| WO | 2010/120548 | 10/2010 |
| WO | 2010/127040 | 11/2010 |
| WO | 2011/136940 | 11/2011 |
| WO | 2011/149693 | 12/2011 |

OTHER PUBLICATIONS

Branched and Fenestrated Stent-Grafts presentation, Tim Chuter, MD, 15 pages.
Branched Stent-Grafts presentation, Tim Chuter, MD, 24 pages.
Branched Stent-Grafts presentation, Tim Chuter, MD, 2002, 30 pages.
Branched Stent-Grafts presentation, Tim Chuter, MD, 29 pages.
Endovascular AAA Repair presentation, Tim Chuter, MD, 2002, 56 pages.
Endovascular AAA Repair presentation, Tim Chuter, MD, 2002, 44 pages.
Endovascular AAA Repair presentation, Tim Chuter, MD, Division of Vascular Surgery, University of California San Francisco, updated Sep. 2002, Part 1—50 pgs. and Part 2—44pgs.
Extended European Search Report, EU App. No. 11178162.1, dated Jul. 17, 2012, 8pp.
International Search Report completed May 8, 2013, PCT/US2013/027614, dated Feb. 25, 2013.
Extended European Search Report, EU App. No. 13275329, dated Apr. 29, 2014, 7pp.
Office Action, Japanese Patent App. No. 2013-269197, dated Nov. 11, 2014, translation.

* cited by examiner

PROSTHESIS HAVING AN EVERTING PIVOTING FENESTRATION

BACKGROUND OF THE INVENTION

The functional vessels of human and animal bodies, such as blood vessels and ducts, occasionally weaken or even rupture. For example, the aortic wall can weaken, resulting in an aneurysm, or it may develop a tear in one of the layers of the aortic wall resulting in an aortic dissection.

One common surgical intervention for weakened, aneurysmal or ruptured passageways or ducts involves the use of an endoluminal prosthesis to provide some or all of the functionality of the original, healthy passageway or duct and/or preserve any remaining vascular integrity by replacing a length of the existing passageway or duct wall that spans the site of failure or defect. Endoluminal prostheses may be of a unitary construction or may be comprised of multiple prosthetic modules. They also may be a single tubular device or a bifurcated branching device depending on the desired application.

In many cases, however, the damaged or defective portion of the vasculature may include a branch vessel branching from the main vessel. For example, in the case of the abdominal aorta, there are at least three major branch vessels, including the celiac, mesenteric, and renal arteries, as well as others, leading to various other body organs. Thus, when the damaged portion of the vessel includes one or more of these branch vessels, some accommodation must be made to ensure that the prosthesis does not block or hinder blood flow through the branch vessel. In many instances, there may be insufficient healthy tissue in the aorta near the branching vessels to adequately seal a prosthesis without partially or completely blocking one or more of the branching vessels.

SUMMARY

The present disclosure relates to an endoluminal prosthesis, such as a stent graft, that includes one or more fenestrations to accommodate endovascular disease, such as an aneurysm, in cases where one or more side branches are involved. In one aspect, the prosthesis includes fenestrations that are pivotable to accommodate the dynamic geometry of the aortic branches. The use of pivotable fenestrations also allows the design of a family of standard stent grafts for "off-the-shelf" use to accommodate a majority of aneurysm cases involving side branches and reducing the need for customization in many cases.

In one aspect, a prosthesis includes one or more pivotable fenestrations that accommodate the variability associated with patient anatomy, both statically and dynamically. For example, one or more pivotable fenestrations provided on a prosthesis may lie outside the surface plane of the body of the prosthesis and will allow a branch vessel stent, graft or stent-graft that has been placed in the fenestration to pivot into any orientation required to meet and seal the branch vessel device in the branch vessel.

The pivotable fenestrations may include an inner perimeter surrounding the fenestration (the hole) in the graft, a band of material surrounding the inner perimeter and extending radially outwardly from the surface plane of the prosthesis, and an outer perimeter surrounding the band of material where the band joins the surface of the prosthesis. The band of material extending from the surface of the prosthesis is sufficiently flexible to permit the fenestration to move such that a branch stent disposed in the fenestration may be oriented upwardly, downwardly, laterally, diagonally and the like. Hence, a device of a single geometry may accommodate a variety of patient anatomies.

In a further aspect, the inner perimeter, the band of material, and the outer perimeter may have a geometric shape and include a support frame disposed about a surface of the band of material. In one embodiment, the support frame includes a plurality of support units having curved segments interconnected by a plurality of apices; a circular reinforcement member disposed on an end of the support frame; and at least one flange positioned on an end of the support frame opposite of the reinforcement member. The curved segments may curve radially outward and away from a longitudinal axis of the prosthesis. The curved segments may have a generally concave configuration with respect to the exterior surface of the prosthesis. The support frame may also include a flange. In some embodiments, the flange may be comprised of a portion of a curved segment and at least one apex. In some embodiments, the support frame is monostable. The band of material may have a depth relative to the surface plane of the prosthesis. The prosthesis may include one stent that is positioned in an out-of-phase configuration with the remaining stents. The inner perimeter, the band, and the outer perimeter of the pivotable fenestration may be at least partially demarcated by the struts of a stent positioned on the body of the stent graft. The support frame may, in some embodiments, comprise helical support units.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

DETAILED DESCRIPTION

Figure 1:
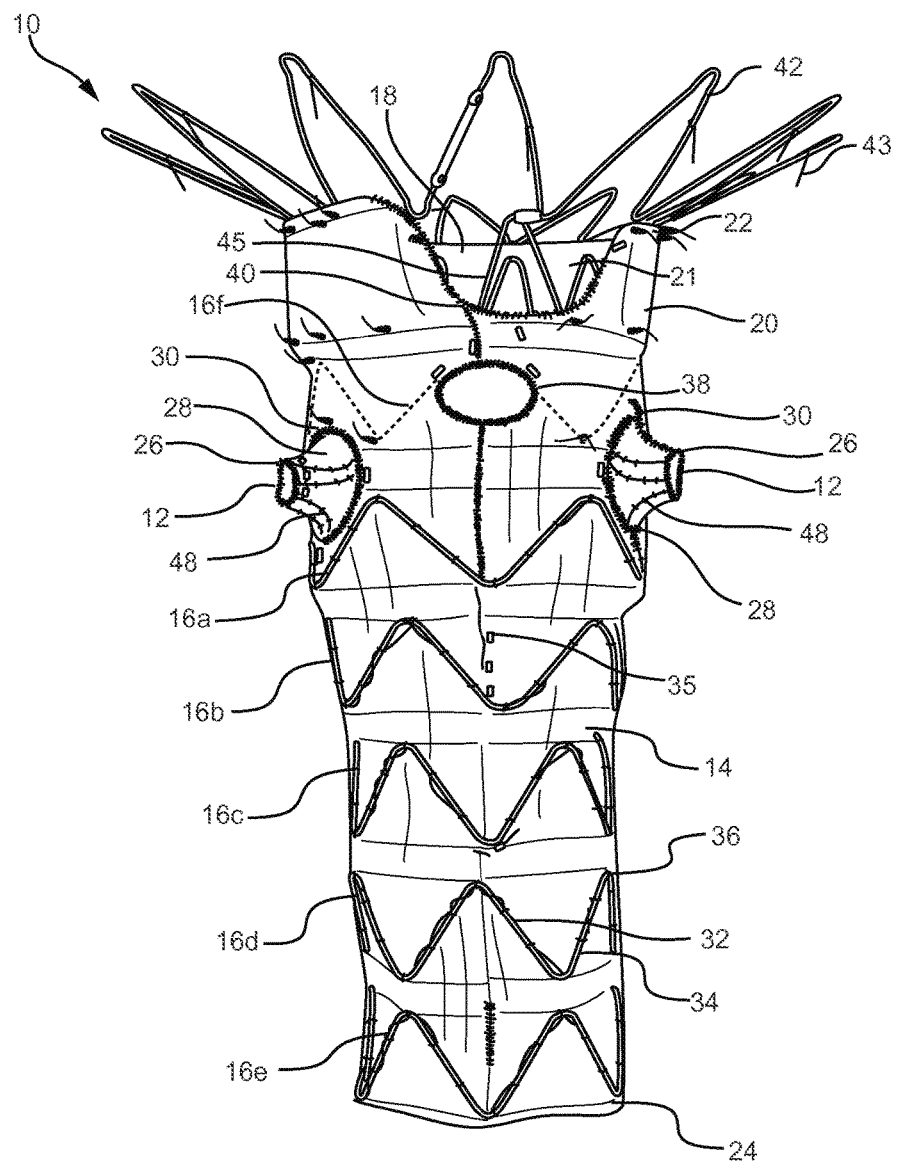
FIG. 1 shows an embodiment of a fenestrated prosthesis having everting pivotable fenestrations.

The present disclosure relates to an endoluminal prosthesis, such as a stent graft that includes one or more fenestrations to accommodate endovascular disease, such as an aneurysm in cases where one or more side branches are involved, and a side branch prosthesis is deployed within the fenestration to permit fluid flow from the endoluminal prosthesis into the branch vessel. The prosthesis includes fenestrations that pivot as needed to accommodate the dynamic geometry of the aortic branches. In various aspects shown and described in more detail below, for example, one or more pivotable fenestrations provided on a prosthesis lie outside the surface plane of the body of the prosthesis and will allow a branch vessel stent, graft or stent-graft that has been placed in the fenestration to pivot into a variety of orientations required to meet and seal the branch vessel device in the branch vessel. The orientation of the fenestrations may dynamically change over time as needed by changing anatomy.

Definitions

Unless defined otherwise, all technical and scientific terms used herein have the same meaning as commonly understood to one of ordinary skill in the art to which this invention belongs.

The term "distal" means a location or direction that is, or a portion of a device that when implanted is further downstream in the direction of or with respect to blood flow.

The term "proximal" means a location or direction that is, or a portion of a device that when implanted is further upstream in the direction of or with respect to blood flow.

The term "fenestration" means an opening provided through a surface of a prosthesis from the interior of the prosthesis to the exterior of the prosthesis and may have a variety of geometries, including circular, semi-circular, oval, oblong, as well as other geometries.

The term "biocompatible" refers to a material that is substantially non-toxic in the in vivo environment of its intended use, and that is not substantially rejected by the patient's physiological system (i.e., is non-antigenic). Examples of biocompatible materials from which textile graft material can be formed include, without limitation, polyesters, such as polyethylene terephthalate, fluorinated polymers, such as polytetrafluoroethylene (PTFE) and fibers of expanded PTFE, and polyurethanes. In addition, materials that are not inherently biocompatible may be subjected to surface modifications in order to render the materials biocompatible. Examples of surface modifications include graft polymerization of biocompatible polymers on the materials surface, coating of the surface with a cross-linked biocompatible polymer, chemical modification with biocompatible functional groups, and immobilization of a compatibilizing agent such as heparin or other biocompatible substances. Thus, any fibrous material having sufficient strength to survive in the in vivo environment may be used to form a textile graft, provided the final textile is biocompatible. Fibers suitable for making textile grafts include polyethylene, polypropylene, polyaramids, polyacrylonitrile, nylon, and cellulose, in addition to the polyesters, fluorinated polymers, and polyurethanes as listed above. Furthermore, bioremodelable materials may also be used singly or in combination with the aforementioned polymer materials. The textile may be made of one or more polymers that do not require treatment or modification to be biocompatible. The graft may be constructed from woven multifilament polyester, for example and without limitation, Dacron™, produced by DuPONT. Dacron™ is known to be sufficiently biologically inert, non-biodegradable, and durable to permit safe insertion inside the human body.

The term "prosthesis" means any device for insertion or implantation into or replacement for a body part or function of that body part. It may also mean a device that enhances or adds functionality to a physiological system. The term prosthesis may include, for example and without limitation, a stent, stent-graft, filter, valve, balloon, embolization coil, and the like.

The term "tubular" refers to the general shape of an endoluminal device which allows the module to carry fluid along a distance or fit within a tubular structure such as an artery. Tubular prosthetic devices include single, branched, and bifurcated devices. Tubular may refer to any shape including, but not limited to, tapered, cylindrical, curvilinear, or any combination thereof. A tubular device may have a cross-sectional shape that is, circular, substantially circular or the like. However, it should be understood that the cross-sectional shape is not limited thereto, and other shapes, such as, for example, hexagonal, pentagonal, octagonal, or the like are contemplated. The term "endoluminal" refers to or describes objects that can be placed inside a lumen or a body passageway in a human or animal body. A lumen or a body passageway can be an existing lumen or a lumen created by surgical intervention. As used in this specification, the terms "lumen" or "body passageway" are intended to have a broad meaning and encompass any duct (e.g., natural or iatrogenic) within the human body and can include a member selected from the group comprising: blood vessels, respiratory ducts, gastrointestinal ducts, and the like. "Endoluminal device" or "endoluminal prosthesis" thus describes devices that can be placed inside one of these lumens.

The term "graft" or "graft material" describes an object, device, or structure that is joined to or that is capable of being joined to or implanted in or against a body part to enhance, repair, or replace a portion or a function of that body part. A graft by itself or with the addition of other elements, such as structural components, may comprise an endoluminal prosthesis. The graft may be comprised of a single material, a blend of materials, a weave, a laminate, or a composite of two or more materials. The graft may be constructed from natural or organic materials, for example and without limitation, a biological scaffold or bioremodelable material, such as small intestine submucosa ("SIS"), which is commercially available by Cook Biotech, West Lafayette, Ind. The graft may also be constructed from a synthetic material, for example and without limitation, a polymer. The graft may be formed from a single layer or multiple layers of material. In embodiments employing a plurality of layers of material, the layers may remain separate, or may be attached to each other through a secondary process such as sintering, curing, adhesives, and sutures or the like.

The term "stent" means any device or structure that adds rigidity, expansion force or support to a prosthesis. A stent is used to obtain and maintain the patency of the body passageway while maintaining the integrity of the passageway. Also, the stent may be used to form a seal. The stent may be located on the exterior of the device, the interior of the device, or both. A stent may be self-expanding, balloon-expandable or may have characteristics of both. A variety of other stent configurations are also contemplated by the use of the term "stent." The stents may be comprised of a metallic material selected from stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, a molybdenum alloy including about 0.4% to about 0.8% of lanthanum oxide ($Li_2O_3$), and a nickel-titanium alloy, such as Nitinol, or other suitable materials as known in the art. The stents may be made of a wire, or may be laser or cannula cut, or manufactured by other known methods.

The term "branch vessel" refers to a vessel that branches off from a main vessel. Examples are the celiac and renal arteries which are branch vessels to the aorta (i.e., the main vessel in this context). As another example, the hypogastric artery is a branch vessel to the common iliac, which is a main vessel in this context. Thus, it should be seen that "branch vessel" and "main vessel" are relative terms.

"Longitudinally" refers to a direction, position or length substantially parallel with a longitudinal axis of a reference.

"Circumferentially" refers to a direction, position, or length that encircles a longitudinal axis of reference. The term "circumferential" is not restricted to a full 360° circumferential turn or to a constant radius.

The terms "patient," "subject," and "recipient" as used in this application refer to any animal, especially humans.

The figures show a fenestrated prosthesis 10, here a stent graft, having a tubular body and comprising a biocompatible material, having one or more fenestrations 12 pivotable in a direction away from an axis perpendicular to a longitudinal axis of the prosthesis. For example, the fenestrations 12 may be pivotable in any direction away from an axis perpendicular to a longitudinal axis of the prosthesis 10. The pivotable fenestrations 12 include a first, inner perimeter 26 surrounding the fenestration 12 having a diameter, a band 28 of flexible material attached to and surrounding the first perimeter 26, and a second, outer perimeter 30 attached to and surrounding the band 28 of flexible material. The band 28 of material has a first diameter that is substantially the same as the diameter of the first perimeter 26, and a second diameter substantially the same as the second perimeter 30. The diameter of the band of material decreases in a direction away from the surface 20 of the graft 14 from the second perimeter to the first perimeter. The band 28 of flexible material includes a support frame 48 having a plurality of support units disposed about a surface of the band 28. In a deployed position, the pivotable fenestrations 12 have an everted configuration with respect to a surface of the prosthesis 10 and have a diameter extending from a side wall of the graft forming a geometric shape. The fenestration 12 may be disposed at the apex of the geometric shape.

In some aspects, the prosthesis 10 is intended for placement in the abdominal aorta and to accommodate vessels that branch from the aorta, for example, the renal arteries, and into which a branch vessel prosthesis may be placed. However, the prosthesis 10 is not limited for use in the abdominal aorta but may be used in other vessels of the body from which other vessels branch, such as the ascending thoracic aorta, the descending thoracic aorta, as well as other body vessels.

FIG. 1 shows an embodiment of a prosthesis 10 that is a stent graft. The prosthesis 10 includes graft material 14 associated with one or more stents 16. The prosthesis 10 has a proximal end 22, a distal end 24, and a lumen 18 extending through the prosthesis 10 to permit passage of blood flow from the proximal end 22 to the distal end 24. The stents 16 may be placed on the external surface 20 and/or internal surface 21 of the graft material 14. In one particular embodiment, the prosthesis 10, such as that shown in FIG. 1, has external body stents 16a, 16b, 16c, 16d and 16e, and at least one internal stent 16f. Additionally, or alternatively, depending on the location of the place of the prosthesis 10 or a particular need, a sealing stent 45 may be placed at either or both the proximal and distal ends 22, 24 of the prosthesis 10. The prosthesis 10 also may include an attachment mechanism, for example, an attachment stent 42, at either or both ends of the prosthesis 10, to further secure the prosthesis 10 within the body vessel and prevent migration of the prosthesis 10. The attachment stent 42 includes barbs 43 that may assist with securing the prosthesis 10 within the target vessel.

The prosthesis 10 has several openings or fenestrations that extend from the internal surface 21 to the external surface 20 of the graft material 14. The prosthesis 10 of FIG. 1 has two pivotable fenestrations 12, at least one non-pivotable fenestration 38, and a scallop 40. Here, the scallop 40 is placed at the proximal end of the prosthesis 10. As shown in greater detail in FIG. 2, the pivotable fenestration 12 has an inner perimeter 26 surrounding the fenestration 12, a band 28 surrounding the inner perimeter 26, and an outer perimeter 30 surrounding the band 28. The outer perimeter 30 diameter is greater than the band 28 diameter and the inner perimeter diameter 26. The inner perimeter 26, the band 28 and the outer perimeter 30 would be substantially concentric with one another if they were in the same plane, for example the surface plane of the graft. The inner perimeter 26, the band 28 and the outer perimeter 30 may form a geometric shape, resembling, for instance, a frustoconical cone extending from the surface of the graft material 14. The fenestration 12 is provided at the peak or top of the geometric shape. In other embodiments, the band 28 may comprise a tapered, flexible tube extending from the outer perimeter 30 and the inner diameter 26. In this embodiment, the pivotable fenestrations 12 have a generally circular configuration. In alternative embodiments, the pivotable fenestrations 12 may have other suitable configurations, including, but not limited to, oblong, oval, rectangular, or triangular. A support frame 48 having a plurality of support units 50 surrounds the fenestration 12 and is positioned on a surface of the band 28. In the embodiment shown in FIGS. 1 and 2, the frame is positioned on the outer surface of the band 28. In other embodiments, the frame may be positioned on an inner surface of the band 28.

Figure 2:
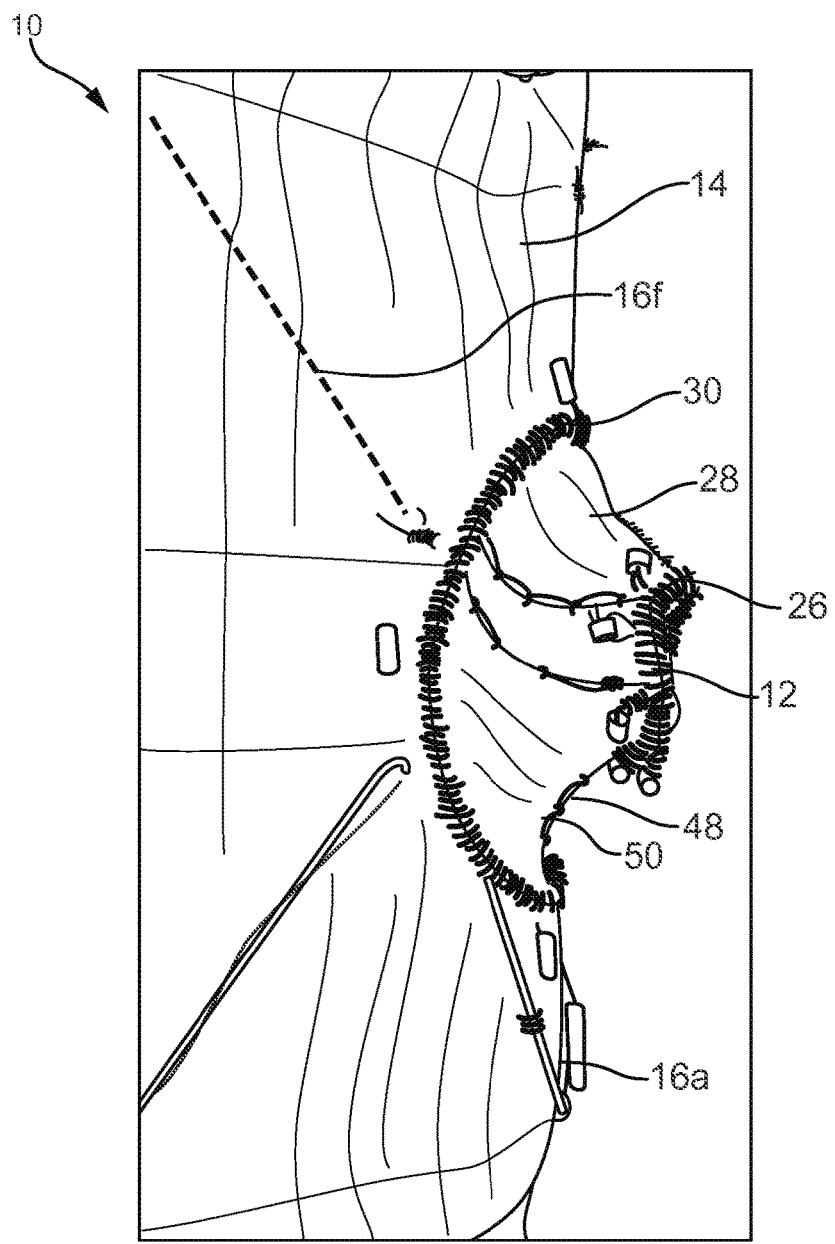
FIG. 2 shows an enlarged view of a pivotable fenestration shown in FIG. 1.

As shown by FIGS. 1 and 2, the pivotable fenestration 12 has an everting configuration with respect to the surface of the prosthesis 10. As used throughout this specification, the term "everting" means extending or protruding radially outward from a surface of the graft material 14. The term "inverting" means extending or protruding radially inward from a surface of the graft material. The outer perimeter 30 lies substantially flush (in the same plane) of the graft material 14, and the band 28 and the outer perimeter 30 form a geometric shape, such as a dome, or frustoconical cone extending outward from the surface of the prosthesis 10. As will be discussed below, the support units 50 of the support frame 48 help to maintain the pivotable fenestration 12 in the everting configuration when the prosthesis 10 is deployed in a patient and prevent the pivotable fenestration 12 from inverting. The pivotable fenestrations 12 are positioned to align with, for example, the renal arteries of a patient. In other aspects, the one or more pivotable fenestrations 12 may be positioned to align with other branch arteries throughout a diseased vasculature. Additional fenestrations and scallops as disclosed here may also be included. As shown in these Figures and throughout the Figures, imageable markers 35, which may be viewed during and after placement of the prosthesis 10 may be placed at various locations on the prosthesis 10 to identify certain aspects of the prosthesis and their location during the implantation procedure and facilitate correct placement of the fenestrations 12, 38, scallop 40, the ends of the prosthesis and the like.

In some embodiments, the outer perimeter 30 surrounding the band 28 may be attached to the graft material 14 by a suitable attachment method including suturing circumferentially about an aperture disposed through graft material 14. In alternative embodiments, inner perimeter 26, band 28, and the outer perimeter 30 may be integral with and formed from the graft material 14 of the prosthesis 10 by creating a protrusion, as described in co-pending U.S. patent application Ser. No. 12/548,120, herein incorporated by reference. The band 28 may be comprised of the same or different biocompatible material as the graft material 14. For example, the biocompatible material of the band 28 may have greater pliability than the first biocompatible graft material used for the tubular graft body. The band 28 is sufficiently flexible to permit the fenestration 12 to move such that a branch stent disposed in the fenestration 12 may be oriented upwardly, downwardly, laterally, diagonally and the like. In some embodiments, the band has up to about 180 degrees of freedom of movement relative to the surface plane of the prosthesis 10. In other embodiments, the band may have greater than 180 degrees of freedom of movement or less than 180 degrees of freedom of movement. Accordingly, the pivotable fenestration 12 allows the prosthesis 10 to be used with a variety of patients, due to its ability to adapt to the variance in the positioning of the diseased branch vessels. For example, if a body branch vessel is or becomes offset longitudinally or axially from a pivoting fenestration 12, the pivoting fenestration 12 may pivot the branch vessel prosthesis in the necessary direction and to the necessary degree to maintain the branch vessel prosthesis in place in the branch vessel.

The band 28 may be tapered such that the diameter decreases throughout its depth. The depth of the band 28 may range from 3 to 10 mm, and preferably is about 6 mm. The inner perimeter 26 has a diameter that is smaller than the diameter of the outer perimeter 30. The diameter of the inner perimeter 26 may be determined based on the average size of the targeted branch vessel. In this aspect, the prosthesis 10 may be used to repair a diseased renal artery. Accordingly, the average diameter of the inner perimeter 26 may be based on the average of the diameter of the openings to the renal arteries, or about 6 mm. The diameter of the outer perimeter 30 may be determined based on the desired amount of movement and the desired patency of the prosthesis 10. The diameters of the inner perimeter 26 and the outer perimeter 30, combined with depth of the band 28, provide the requisite amount of surface area for the pivotable fenestration 12 to pivot during deployment of a secondary branch prosthesis into the fenestration 12 based on dynamic changes to the anatomy. Reinforcement members may be attached to the graft 14 surrounding the outer perimeter of the pivotable fenestrations 12. In addition, reinforcement members may be provided about the perimeter of the non-pivoting fenestration 38, and the perimeter of the scallop 40, respectively. In one preferred aspect, the reinforcement members comprise a wire that is sutured about the fenestration 12, 38, or scallop 40, to reinforce the fenestration or scallop. The reinforcement members may be made of any suitable material. One preferred material is a superelastic or shape memory material, such as Nitinol. In another preferred embodiment, the reinforcement members may be made of radiopaque or other imageable material. In another embodiment the reinforcement members may be a wire that is looped about itself into a ring with unattached ends such that the ring may be expanded or contracted in diameter, such as described in co-pending U.S. patent application Ser. No. 10/962,632, herein incorporated by reference.

Figure 3:
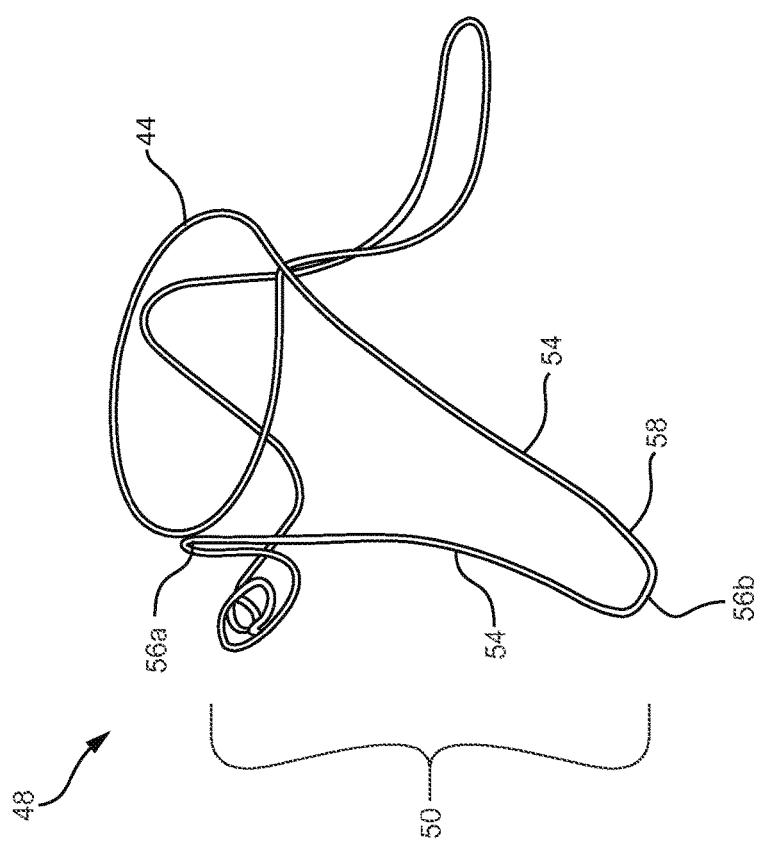
FIG. 3 shows a perspective view of a support frame for a fenestrated prosthesis having everting pivotable fenestrations shown in FIG. 1.

FIG. 3 shows an embodiment of the support frame 48. In a preferred aspect, the support frame 48 is a continuous wire formed into a plurality of support units 50 comprising curved segments 54 having a generally concave configuration with respect to the exterior surface 20 of the prosthesis 10 joined by apices 56*a* and 56*b* and a circular, reinforcement member 44. The reinforcement member 44 is configured to be positioned about the inner perimeter 26 of the pivotable fenestrations 12. As shown in this embodiment, the support frame 48 has three support units 50. Apices 56*a* are positioned adjacent to the reinforcement member 44. The ends of the concave, curved segments 54 and apices 56*b* form a flange 58 positioned on an end of the support frame 48 opposite of the reinforcement member 44. The flange 58 may abut or connect to the reinforcing member 44 positioned about the outer perimeter 30 of the pivotable fenestration 12. The flange 58 is configured to lie generally against a surface of the band 28 and help facilitate attachment of the frame 48 to the band 28. The concave, curved segments 54 of the support members 50 generally curve radially outward and away from a surface of the prosthesis 10. As such, the support units 50 are configured to extend radially outward from the surface of the prosthesis 10 when positioned on the band 28 of the pivotable fenestration 12. The support frame 48 is generally monostable, which means that the frame will always return to its expanded, resting configuration upon removal of any compression or restraint, which prevents the support frame 48 from inverting. While not being held to any theory, it is believed that the concave, curved segments 54 of the support units 50 of the support frame 48 help prevent any inversion of the frame. As such, the support frame 48 helps bias the pivotable fenestration 12 into an everting configuration with respect to a surface of the prosthesis 10 and prevents the pivotable fenestration 12 from protruding into the lumen of the prosthesis 10. In addition, the pivotable fenestration 12 having an everting configuration provides flexibility to ensure compatibility with an array of patient vessel locations. While the support frame 48 of this embodiment is comprised of a single, continuous wire, alternative embodiments of the support frame 48 may comprise a plurality of wire segments joined together to form the support units 50 and desired configuration of the support frame 48. In addition, alternative embodiments of the support frame 48 may comprise a continuous wire formed into one or more support units having a generally coiled helical configuration.

Referring back to FIG. 1, stents 16 may be configured in the form of one or more "Z-stents", each of which may comprise a series of substantially straight segments 32 interconnected by a series of bent segments 36. The bent segments may comprise acute bends or apices. The stents are arranged in a zigzag configuration in which the straight segments 32, 34 are set at angles relative to each other and are connected by the bent segments. However, the stents 16 may comprise any suitable configuration and one or more stents 16 may be provided. When Z-stents are used, a portion of the outer perimeter 30 of one or more of the fenestrations 12 may lie between adjacent struts 32, 34 of one of the stents 16. The stents 16 may be either self-expanding or balloon expandable. Preferably, they are self-expanding. However, a combination of self-expanding and balloon expandable stents 16 also may be contemplated.

Stent amplitude, spacing and stagger are preferably optimized for each prosthesis design. In some aspects, the apices or bends 36 of the struts 32, 34 may be staggered for minimal contact with each other. As shown in FIG. 1, the stents 16a, 16b, and 16c are positioned adjacent each other and the apices 36 of each row are in circumferential alignment or "in phase", with the apices of longitudinally adjacent rows. In addition, stent 16e is also positioned in phase with stents 16a, 16b, and 16c. Stent 16d is positioned "out of phase" by about 180 degrees with longitudinally adjacent row 16c, such that circumferentially about the surface of the graft, every other apex of the stent 16c matches with every other apex of stent row 16d. In other embodiments, the stent 16d may be positioned in phase with longitudinally adjacent row 16c, or the stent 16d may be out of phase with stent 16c by an amount less than 180 degrees. Furthermore, internal stent 16f is positioned out of phase by about 180 degrees with longitudinally adjacent row 16a, such that circumferentially about the surface of the graft, every other apex of the stent 16a matches with every other apex of stent row 16e. In other embodiments, the stent 16f may be positioned in phase with longitudinally adjacent row 16a, or the internal stent 16f may be out of phase with stent 16a by an amount less than 180 degrees. In an exemplary embodiment, the inner perimeter 26, the band 28, and the outer perimeter 30 of the pivoting fenestration 12 are demarcated by a pair of longitudinally adjacent struts of internal stent 16f and stent 16a, respectively. In this embodiment, the area of the prosthesis 10 located between the internal stent 16f, which is out of phase, and the stent 16a provides additional space for the movement of the band 28 of the pivoting fenestration 12, which allows for increased flexibility for the pivoting fenestration 12.

Figure 4:
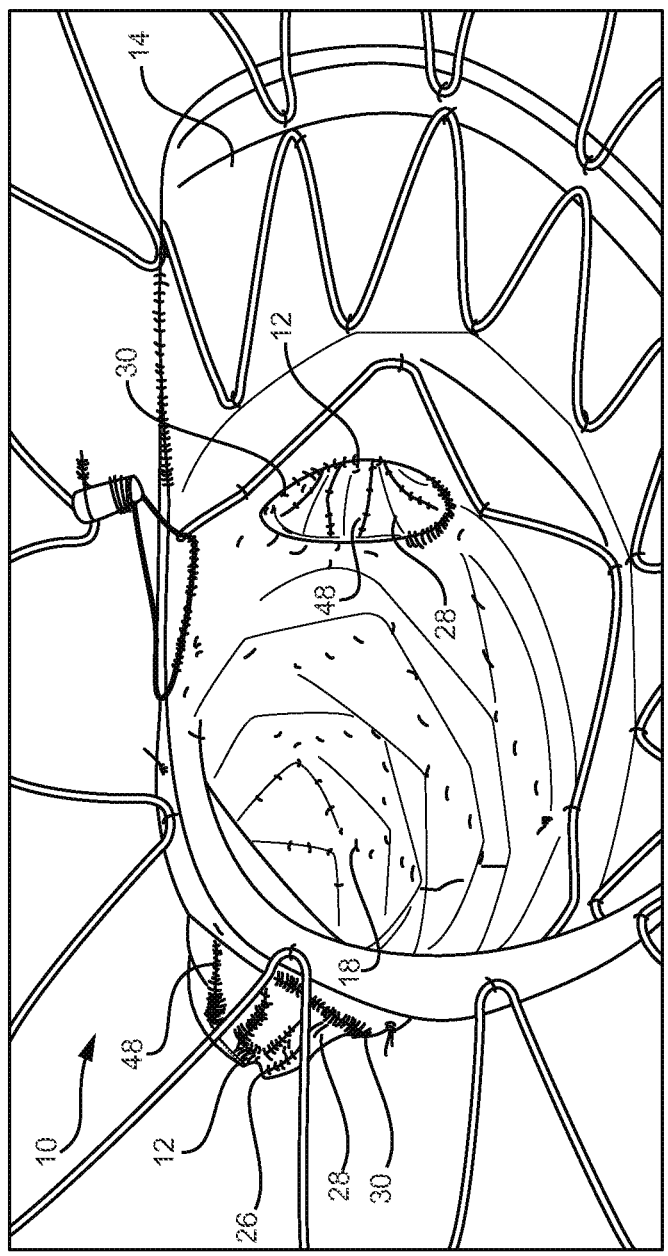
FIG. 4 is a partial and internal view of the prosthesis as shown in FIG. 1.

FIG. 4, which is a partial internal view of the prosthesis 10 of FIG. 1, shows a view of the prosthesis 10 looking into the lumen 18 of the prosthesis 10 from the proximal end 22. As shown, pivotable fenestrations 12 are in fluid communication with the lumen 18. The outer perimeter 30 lies substantially flush (in the same plane) of the graft material 14, and the band 28 and the outer perimeter 30 form a geometric, frustoconical cone shape extending outward from the lumen 18 of the prosthesis 10. In this embodiment, the pivotable fenestrations 12 are not disposed within the lumen 18 of the prosthesis 10 and fail to protrude within the lumen of the prosthesis. The prosthesis 10 has a clear lumen 18 once the prosthesis 10 is deployed, and minimizes the possibility of blood flow through the lumen 18 being interrupted by the pivotable fenestration 12. The pivotable fenestration 12 having an everting configuration also allows for additional room for the placement of medical devices through the fenestration to minimize the disruption to blood flow. For example, when a covered stent is placed within the pivotable fenestration 12, the lumen extension of the covered stent has additional room to minimize disruption to blood flow.

Figure 5A:
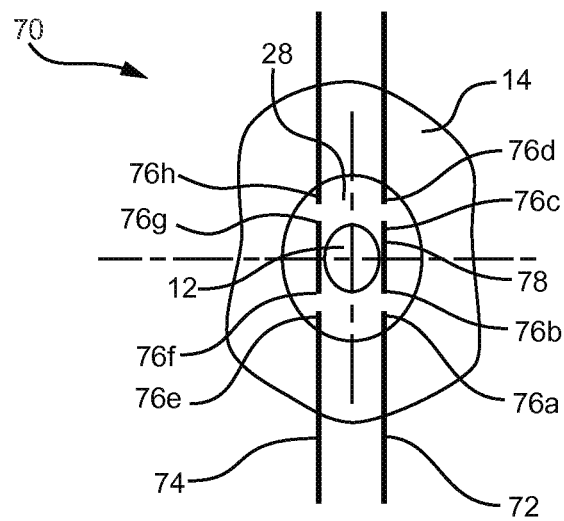
FIG. 5a shows a view from within the lumen of an embodiment of a fenestrated prosthesis having an embodiment of a retention assembly for restraining everting pivotable fenestrations of a fenestrated device.
Figure 5B:
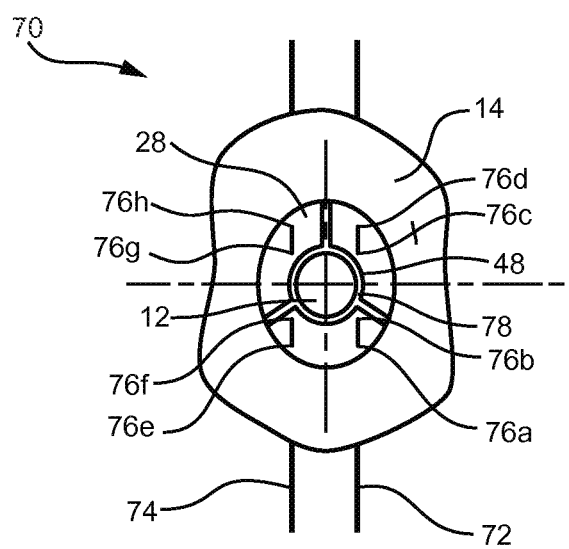
FIG. 5b shows a view from the exterior of an embodiment of a fenestrated prosthesis having an embodiment of a retention assembly for restraining everting pivotable fenestrations of a fenestrated device.
Figure 5C:
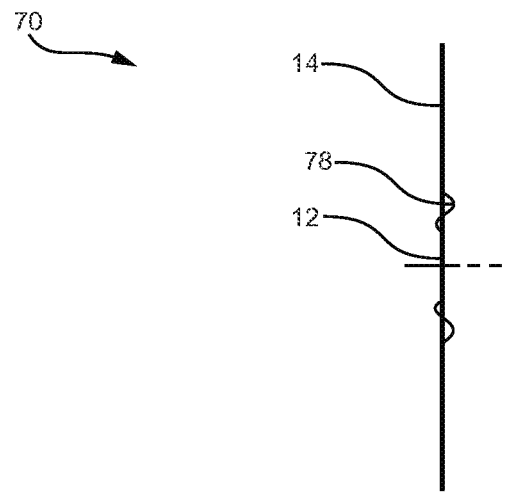
FIG. 5c shows a side cross-sectional view of an embodiment of a fenestrated prosthesis having an embodiment of a retention assembly for restraining everting pivotable fenestrations of a fenestrated device.

FIGS. 5a-5c show an embodiment of a retention assembly 70 for the pivotable fenestration 12 of the prosthesis 10. The retention system 70 includes trigger wires 72 and 74. FIG. 5a and FIG. 5b show views from the interior and the exterior of the prosthesis 10, respectively. As shown trigger wires 72 and 74 extend from within the lumen of the prosthesis 10. The trigger wires 72 and 74 are configured to extend through the length of the prosthesis 10. The trigger wires 72 and 74 engage with the band 28 of pivoting fenestration 12. In order to facilitate engagement of the trigger wires 72 and 74 through the band 28 a plurality of apertures 76a-76h are disposed through the surface of the band 28. In particular, trigger wire 72 exits the lumen of the prosthesis 10 through aperture 76a and re-enters into the lumen through aperture 76b. Trigger wire 72 also exits the lumen of the prosthesis 10 through aperture 76c and re-enters into the lumen through aperture 76d. Similarly, trigger wire 74 exits the lumen of the prosthesis 10 through aperture 76e and re-enters into the lumen through aperture 76f. Trigger wire 74 also exits the lumen of the prosthesis 10 through aperture 76g and re-enters into the lumen through aperture 76h. The trigger wires 72 and 74 form a plurality of segments 78 on an interior surface and an exterior surface of the band 28. As shown in FIG. 5a, the trigger wires 72 and 74 form one segment 78 on the interior surface of the band 28. As shown in FIG. 5b, the trigger wires 72 and 74 form two segments 78 on the exterior surface of the band 28. In addition, the segments 78 on the exterior surface of the band 28 are positioned such that they avoid coming into contact with the support frame 48 of the pivotable fenestration 12. As shown, the trigger wires 72 and 74 do not engage the graft material 14 surrounding the band 28. When the pivotable fenestrations 12 are restrained by the trigger wires 72 and 74, the pivotable fenestrations 12 lie on the same plane as a sidewall of the prosthesis 10, as shown in FIG. 5c. The trigger wires 72 and 74 may be placed in the configuration shown in the figures upon placement within a delivery device for the prosthesis 10. Upon removal of the trigger wires 72 and 74, the pivoting fenestration 12 is deployed within the targeted vessel and the support frame 48 expands and the pivotable fenestration 12 is positioned in the everting configuration.

Figure 6A:
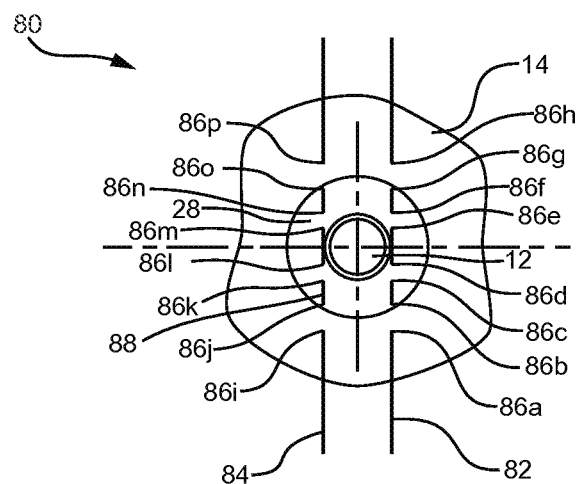
FIG. 6a shows a view from within the lumen of an embodiment of a fenestrated prosthesis having an alternative embodiment of a retention assembly for restraining everting pivotable fenestrations of a fenestrated device.
Figure 6B:
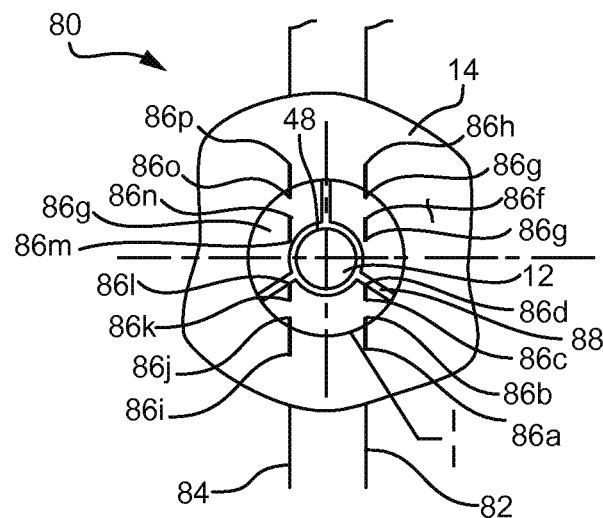
FIG. 6b shows a view from the exterior of an embodiment of a fenestrated prosthesis having an alternative embodiment of a retention assembly for restraining everting pivotable fenestrations of a fenestrated device.
Figure 6C:
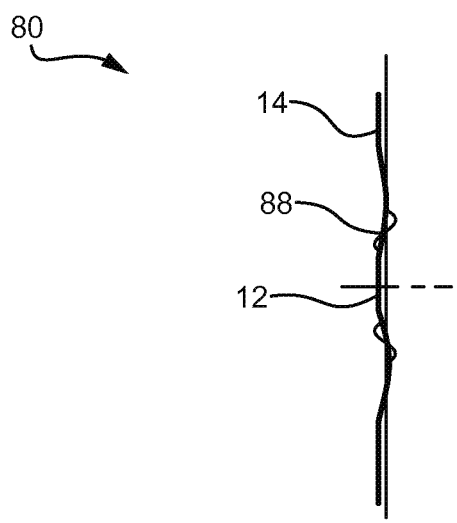
FIG. 6c shows a side cross-sectional view of an embodiment of a fenestrated prosthesis having an alternative embodiment of a retention assembly for restraining everting pivotable fenestrations of a fenestrated device.

FIGS. 6a-6c show an alternative embodiment of a retention assembly 80 for the pivotable fenestration 12 of the prosthesis 10. FIG. 6a and FIG. 6b show views from the interior and the exterior of the prosthesis 10, respectively. The retention system 80 includes trigger wires 82 and 84. As shown, trigger wires 82 and 84 are from within the lumen of the prosthesis 10. The trigger wires 82 and 84 are configured to extend through the length of the prosthesis 10. The trigger wires 82 and 84 engage with the band 28 of pivoting fenestration 12. In order to facilitate engagement of the trigger wires 82 and 84 through the band 28 a plurality of apertures 86a-86p are disposed through the surface of the band 28 and the graft material 14 surrounding the band 28. In particular, trigger wire 82 exits the lumen of the prosthesis 10 through aperture 86a and re-enters into the lumen through aperture 86b. Trigger wire 82 also exits the lumen of the prosthesis 10 through aperture 86c and re-enters into the lumen through aperture 86d. Trigger wire 82 also exits the lumen of the prosthesis 10 through aperture 86c and re-enters into the lumen through aperture 86d; exits the lumen of the prosthesis 10 through aperture 86e and re-enters into the lumen through aperture 86f; and exits the lumen of the prosthesis 10 through aperture 86g and re-enters into the lumen through aperture 86h. Similarly, trigger wire 84 exits the lumen of the prosthesis 10 through aperture 86i and re-enters into the lumen through aperture 86j. Trigger wire 84 also exits the lumen of the prosthesis 10 through aperture 86k and re-enters into the lumen through aperture 86l; exits the lumen of the prosthesis 10 through aperture 86m and re-enters into the lumen through aperture 86n; and exits the lumen of the prosthesis 10 through aperture 86o and re-enters into the lumen through aperture 86p. The trigger wires 82 and 84 form a plurality of segments 88 on an interior surface and an exterior surface of the band 28. As shown in FIG. 6a, the trigger wires 82 and 84 form one segment 88 on the interior surface of the band 28. As shown in FIG. 6b, the trigger wires 82 and 84 form two segments 78 on the exterior surface of the band 28. In addition, the segments 88 on the exterior surface of the band 28 are positioned such that they avoid coming into contact with the support frame 48 of the pivotable fenestration 12. When the pivotable fenestrations 12 are restrained by the trigger wires 82 and 84, the pivotable fenestrations 12 lie on the same plane as a sidewall of the prosthesis 10, as shown in FIG. 6c. The trigger wires 82 and 84 may be placed in the configuration shown in the figures upon placement within a delivery device for the prosthesis 10. Upon removal of the trigger wires 82 and 84, the pivoting fenestration 12 is deployed within the targeted vessel and the support frame 48 expands and the pivotable fenestration 12 is positioned in the everting configuration.

The restrained configuration of the pivotable fenestration 12 allows abluminal clearance between the device and a patient's branch vessel to ease cannulation. While this embodiment shows two trigger wires, other embodiments may comprise fewer trigger wires or more trigger wires to constrain the pivotable fenestrations 12. For example, one embodiment may use one trigger wire to constrain the pivotable fenestrations 12, which may reduce the width of the prosthesis 10 and provide additional space to cannulate the branch vessels. In addition, in other embodiments, the trigger wires may restrain the pivotable fenestrations 12 such that they lie in a plane that is within the lumen of the prosthesis 10 prior to deployment of the vessel. In these embodiments, the trigger wires may be slightly biased inward toward a longitudinal axis of the prosthesis 10, in order to allow for support and space for cannulation of a branch vessel.

Figure 7:
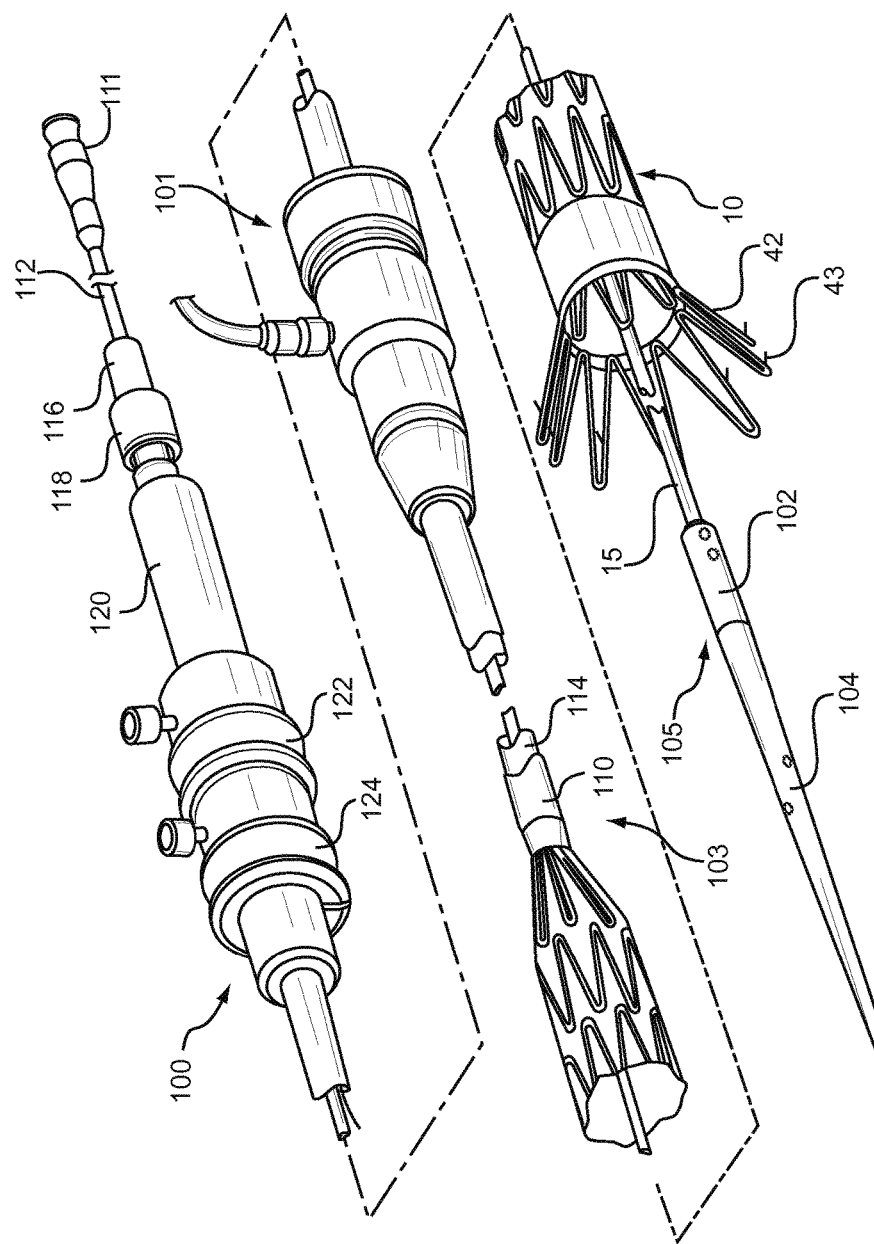
FIG. 7 shows an embodiment of a delivery device used with a retention system for deployment of a fenestrated prosthesis having everting pivotable fenestrations.

The retention systems 70 and 80 may be used with various delivery systems for endoluminal devices, such as that described in U.S. Pat. No. 7,651,519, entitled "Prosthesis Deployment System", and U.S. Pat. No. 7,666,219, entitled "Prosthesis Deployment System Retention Device", which are incorporated herein by reference in their entirety. In the aspect shown in FIG. 7, the delivery system 100 for deploying an endoluminal prosthesis 10 in a vessel of a patient includes an external manipulation section 101, a distal positioning mechanism or attachment region 103, and a proximal positioning mechanism or attachment region 105. The external manipulation section 101, which is acted upon by a user to manipulate the introducer 100, remains outside of the patient throughout the procedure. The proximal attachment region includes a retention device 102. The retention device 102 has at its proximal end a long tapered flexible extension 104, or dilator. A thin walled tube 112 generally made of metal is fastened to the extension 104. The thin walled tube 112 is flexible so that the introducer can advance within a relatively tortuous vessel, such as the femoral artery. The thin walled tube 112 also allows manipulation longitudinally and rotationally of the proximal attachment region 105. The thin walled tube 112 extends throughout the introducer 100 to the manipulation section 101, terminating at a connection means 111. The connection means 111 is adapted to accept a syringe to facilitate the introduction of reagents into the metal tube 112. A tube 114 is coaxial with and radially outside the thin walled tube 112. The tube 114 is "thick walled", which is to say the thickness of the wall of tube 114 is several times that of the thin walled tube 112. A sheath 110 is coaxial with and radially outside the thick walled tube 112.

The external manipulation section 101 has a body 120 that is mounted onto the thick walled plastic tube 114, which passes through the body 120. The pin vice 118 has a screw cap 116. When screwed in, vice jaws (not shown) clamp against and engage the thin walled tube 112, and the thin walled tube 112 can only move with the body 120, and hence can only move with the thick walled tube 114. A proximal wire release mechanism 122 and a distal wire release mechanism 124 are mounted for slideable movement on the body 120. A pin vice 118 is mounted onto the distal end of the body 120. The positioning of the proximal and distal wire release mechanisms 122 and 124 is such that the proximal wire release mechanism 122 must be moved before the distal wire release mechanism 124 can be moved. The retention systems 70 and 80 may be associated with either the proximal wire release mechanism or the distal wire release mechanism.

In use, the operator deploys the delivery device 100 over a guide wire and into the patient through an artery, such as the femoral artery, via an incision and the introducer is extended up into the aortic bifurcation and positioned such that the dilator 104 is proximal of the renal arteries. The sheath 110 is withdrawn such that the prosthesis 10 is exposed. The operator may then position the prosthesis 10 within the vessel such that the pivotable fenestrations 12 are positioned in the vicinity of the branch vessel. Once the prosthesis 10 and the pivotable fenestrations 12 are in the proper position, the operator may cannulate the branch vessels. The pivotable fenestrations remain in the restrained position by the retention mechanism, which allows for adequate space for cannulation. The operator may introduce additional endoluminal prostheses, such as an indwelling catheter for deploying a branch stent into an internal artery, as described, for example, in U.S. Pat. No. 6,524,335, herein incorporated by reference. Following cannulation, the operator may release and remove the trigger wires of the retention system 70 and 80, which allows the support frame 48 of the pivotable fenestration 12 to expand, where the pivotable fenestration 12 has an everted configuration. In this position, the operator may introduce a branch stent into the branch vessel through the pivotable fenestration 12.

Throughout this specification various indications have been given as to preferred and alternative examples and aspects of the invention. However, the foregoing detailed description is to be regarded as illustrative rather than limiting and the invention is not limited to any one of the provided aspects. It should be understood that it is the appended claims, including all equivalents, that are intended to define the spirit and scope of this invention.

The invention claimed is:

1. An endoluminal prosthesis, comprising:
   a graft having a tubular body and a surface comprising a first biocompatible material;
   one or more stents attached about the surface of the graft;
   one or more fenestrations disposed through a sidewall of the graft, each fenestration having a diameter;
   at least one fenestration having a first perimeter having a first diameter and surrounding the fenestration;
   the first perimeter having a band of flexible material attached to and surrounding the first perimeter, the band of flexible material having a depth relative to a surface plane of the tubular body; and
   the band of flexible material having a second perimeter surrounding the band of flexible material; and a support frame attached to and positioned on an outer surface of the band of flexible material and extending between the first perimeter and the second perimeter, the support frame having a monostable structure comprising a flange and one or more support units having curved, concave segments with respect to an exterior surface of the graft and a circular reinforcement member, the one or more support units surrounding the at least one fenestration;

where the first perimeter, the band of flexible material, and the second perimeter have a geometric shape, the geometric shape extending radially outward from a surface of prosthesis and having an everting configuration, and where each fenestration is pivotable in a direction away from an axis perpendicular to a longitudinal axis of the prosthesis.

2. The prosthesis of claim 1, where the support frame comprises at least three support units.

3. The prosthesis of claim 1, where the curved segments of the one or more support units are interconnected by a plurality of apices.

4. The prosthesis of claim 1, wherein the curved segments curve radially outward and away from a longitudinal axis of the prosthesis.

5. The prosthesis of claim 1, where the support units of the support frame are comprised of a single continuous wire.

6. The prosthesis of claim 1, wherein the geometric shape is generally frustoconical.

7. The prosthesis of claim 1, wherein at least one stent is positioned in an out-of-phase configuration, the stents comprising a plurality of struts interconnected by apices.

8. The prosthesis of claim 7, wherein the first perimeter, the band of flexible material, and the second perimeter are at least partially demarcated by a pair of struts on the stent having an out-of-phase configuration.

* * * * *